(12) United States Patent
Nielsen et al.

(10) Patent No.: US 11,418,899 B2
(45) Date of Patent: Aug. 16, 2022

(54) EARPIECE FOR A HEARING DEVICE

(71) Applicant: GN HEARING A/S, Ballerup (DK)

(72) Inventors: Henrik Nielsen, Roskilde (DK); Jan Johansen, Koge (DK)

(73) Assignee: GN HEARING A/S, Ballerup (DK)

( * ) Notice: Subject to any disclaimer, the term of this patent is extended or adjusted under 35 U.S.C. 154(b) by 206 days.

(21) Appl. No.: 16/660,798

(22) Filed: Oct. 22, 2019

(65) Prior Publication Data

US 2020/0196073 A1 Jun. 18, 2020

(30) Foreign Application Priority Data

Dec. 17, 2018 (EP) .................................. 18213126

(51) Int. Cl.
*A61B 5/0205* (2006.01)
*H04R 25/00* (2006.01)
(Continued)

(52) U.S. Cl.
CPC ....... *H04R 25/652* (2013.01); *A61B 5/14552* (2013.01); *A61B 5/6817* (2013.01);
(Continued)

(58) Field of Classification Search
CPC . A61B 5/0082; A61B 5/0205; A61B 5/14552; A61B 5/398; A61B 5/4076; A61B 5/6817; A61B 5/291; A61B 5/415; A61B 5/6803; A61B 5/02055; A61B 5/30; A61B 5/369; A61B 7/003; G06F 3/044; H04R 1/1025; H04R 1/1041; H04R 25/554; H04R 25/604; H04R 25/609; H04R 25/652; H04R 2225/025; H04R 1/1016; H04R 25/65; H04R 25/55; H04R 25/607; H04R 25/656;
(Continued)

(56) References Cited

U.S. PATENT DOCUMENTS 8,157,730 B2 * 4/2012 LeBoeuf ................ A61B 5/415
600/595
9,746,354 B2 * 8/2017 Martin .................... G01C 19/00
(Continued)

FOREIGN PATENT DOCUMENTS

EP 2 077 091 A2 7/2009
EP 2 077 091 A3 10/2009

OTHER PUBLICATIONS

Extended European Search Report dated Jun. 28, 2019 for corresponding European Application No. 18213126.8.

*Primary Examiner* — Gerald Gauthier
(74) *Attorney, Agent, or Firm* — Vista IP Law Group, LLP

(57) ABSTRACT

An earpiece for a hearing device includes an ear canal part to be introduced into an ear canal of a user, the ear canal part comprising: an earpiece housing comprising a first end configured to be positioned medially inside the ear canal of the user, and a second end configured to be positioned laterally to the ear canal of the user, wherein the earpiece housing comprises a side wall between the first end and the second end; and a primary sensor, wherein the primary sensor is positioned inside a first volume in the earpiece housing; wherein the side wall of the earpiece housing comprises a first pass-through area, and wherein the primary sensor is configured to measure a physiological parameter through the first pass-through area.

29 Claims, 2 Drawing Sheets

(51) Int. Cl.
 *A61B 5/1455* (2006.01)
 *A61B 5/00* (2006.01)
(52) U.S. Cl.
 CPC ......... *H04R 25/604* (2013.01); *H04R 25/609* (2019.05); *H04R 2225/025* (2013.01)
(58) Field of Classification Search
 CPC .. G10K 11/17885; G01C 19/00; G16H 40/63; H01M 50/216
 USPC ....... 381/315, 324, 380, 323, 328, 329, 330; 600/300
 See application file for complete search history.

(56) References Cited

U.S. PATENT DOCUMENTS

| | | | | |
|---|---|---|---|---|
| 9,774,941 | B2* | 9/2017 | Grinker | G10K 11/17885 |
| 9,838,775 | B2 | 12/2017 | Qian et al. | |
| 10,848,848 | B2* | 11/2020 | Stockton, X | A61B 7/003 |
| 10,856,063 | B1* | 12/2020 | Hviid | G06F 3/044 |
| 2003/0002705 | A1* | 1/2003 | Boesen | H04M 1/6066 |
| | | | | 381/380 |
| 2005/0209516 | A1 | 9/2005 | Fraden | |
| 2009/0299215 | A1 | 12/2009 | Zhang | |
| 2010/0177919 | A1* | 7/2010 | Giese | H04R 25/656 |
| | | | | 381/328 |
| 2012/0328139 | A1* | 12/2012 | Naumann | H04R 25/607 |
| | | | | 381/330 |
| 2013/0039519 | A1* | 2/2013 | Kilsgaard | H04R 25/609 |
| | | | | 381/324 |
| 2013/0114838 | A1* | 5/2013 | Berkmann | H01M 50/216 |
| | | | | 381/323 |
| 2014/0153762 | A1* | 6/2014 | Shennib | H04R 25/656 |
| | | | | 381/328 |
| 2016/0081623 | A1* | 3/2016 | Lunner | H04R 25/554 |
| | | | | 381/315 |
| 2017/0095165 | A1 | 4/2017 | Hirano | |
| 2017/0095202 | A1 | 4/2017 | Facteau et al. | |
| 2017/0311097 | A1* | 10/2017 | Nielsen | A61N 1/0541 |
| 2018/0199140 | A1 | 7/2018 | Husung et al. | |
| 2018/0263562 | A1* | 9/2018 | Laplante-Levesque | A61B 5/1107 |
| 2019/0033505 | A1* | 1/2019 | Cross | H04R 25/652 |
| 2019/0174238 | A1* | 6/2019 | Lu | A61B 5/0205 |
| 2019/0253793 | A1* | 8/2019 | Pedersen | H04R 25/55 |
| 2019/0268706 | A1* | 8/2019 | Solum | A61B 5/6815 |
| 2020/0092632 | A1* | 3/2020 | Higgins | H04R 25/607 |
| 2020/0145768 | A1* | 5/2020 | Nielsen | H04R 25/609 |
| 2020/0186904 | A1* | 6/2020 | Krull | H04R 25/652 |
| 2020/0196071 | A1* | 6/2020 | Larsen | H04R 1/028 |
| 2020/0196073 | A1* | 6/2020 | Nielsen | A61B 5/6817 |
| 2020/0261027 | A1* | 8/2020 | Goldstein | A61B 5/6803 |
| 2021/0315740 | A1* | 10/2021 | Lonsky | H04R 25/652 |
| 2022/0118253 | A1* | 4/2022 | Wetmore | G16H 40/63 |

* cited by examiner

EARPIECE FOR A HEARING DEVICE

RELATED APPLICATION DATA

This application claims priority to, and the benefit of, European Patent Application No. 18213126.8 filed on Dec. 17, 2018. The entire disclosure of the above application is expressly incorporated by reference herein.

FIELD

The present disclosure relates to an earpiece for a hearing device

BACKGROUND

There is a general need for devices that are capable of monitoring health data from users at any time, and where it is helpful for healthcare professionals and users to have access to data that may be continuously obtained from the user. A hearing device is a device which is well known to a user, and can either be worn continuously as a hearing aid or intermittently as a headset. Thus, the introduction of monitoring devices into a hearing device may make it easy for the user to provide health data monitoring, while maintaining comfort for the user.

The introduction of health monitoring into an earpiece has been shown in US 2005/0209516 where an earplug is provided using an optical sensor, where the optical sensor is configured to measure a temperature of the user, as well as allowing for accurate computation of various vital signs

SUMMARY

Accordingly, there is a need for earpieces for hearing devices where the earpiece does not put strain on the ear of the user.

An earpiece for a hearing device is disclosed, the earpiece comprising an ear canal part to be introduced into the ear canal of a user, the ear canal part comprising: an earpiece housing comprising a first end configured to be positioned medially inside the ear canal of the user, and a second end configured to be positioned laterally to the ear canal of the user, where the earpiece housing comprises a side wall extending from the first end to the second end, where the side wall at least partly defines a first volume inside the earpiece housing; a primary sensor where the primary sensor is positioned inside the first volume of the earpiece housing; where the side wall of the earpiece housing comprises a first pass-through area, and wherein the primary sensor is configured to measure a physiological parameter through the first pass-through area.

It is an important advantage of the earpiece that the earpiece housing comprises a pass through area, which allows the primary sensor to transmit and/or receive signals inside the ear canal of the user. This means that an earpiece housing, which may be generic or customized for the user may be introduced into the ear canal, where the primary sensor will have a passage of signals to the skin surface of the user. An earpiece housing is often in a shape that corresponds to the structure of the ear canal, and where the earpiece housing is designed to fill out a diameter of the ear canal in order to prevent ambient noise to enter the ear canal, during the use of the earpiece. Thus, the earpiece housing will have a dimension that fills out a cross sectional diameter of the ear canal, which means that the size of the earpiece housing may have a relatively large volume.

Thus, the volume of the earpiece may be larger than what may be necessary to house the components of an earpiece. Thus, by utilizing some of the unused volume of the earpiece to introduce a primary sensor into the earpiece housing, it may be possible to include a sensor inside a volume which is identical to the volume that otherwise would be used for the earpiece.

Also disclosed is a receiver housing for a hearing device, the receiver housing may be configured to be introduced into the ear canal of a user, the receiver housing comprising: a receiver; a primary sensor, wherein the primary sensor is configured to measure a physiological parameter from the ear canal of the user The provision of a receiver housing, where the receiver housing comprises a receiver as well as a primary sensor may mean that the components for both the receiver and the primary sensor may be included in a housing. The integration of the receiver and the primary sensor in the receiver housing may reduce the total volume of components and circuitry inside the housing. A predefined volume of an earpiece housing may be seen as being defined by the structure and shape of the ear canal of the user, as the earpiece housing fills out a part of the volume of the ear canal. By providing a receiving housing in having both a receiver and a primary sensor means that a primary sensor may be introduced into an earpiece having a predefined volume, where the volume used by the receiving housing is similar to the volume already used by a receiver, and does therefore not take up more volume than a conventional receiver would, and will not enlarge the earpiece housing, as it already has a predefined volume, which is limited by anatomical structure of the ear canal.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1:
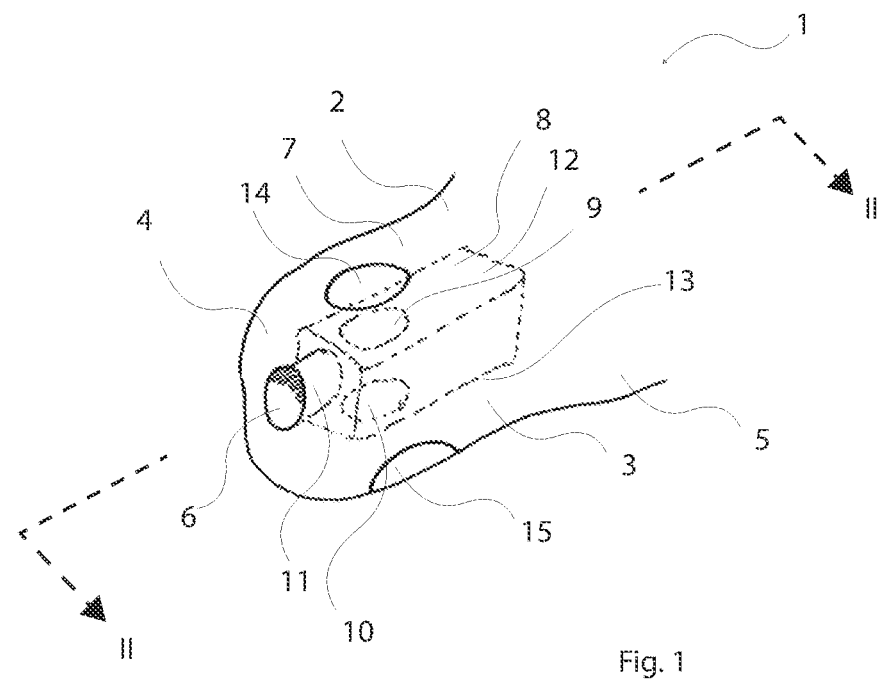
FIG. 1 is a perspective view of an exemplary earpiece.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing device is disclosed. The hearing device may be a hearable or a hearing aid, wherein the processor is configured to compensate for a hearing loss of a user.

The hearing device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid. The hearing device may comprise a first earpiece and a second earpiece, wherein the first earpiece and/or the second earpiece is an earpiece as disclosed herein.

The hearing device may be configured for wireless communication with one or more devices, such as with another hearing device, e.g. as part of a binaural hearing system, and/or with one or more accessory devices, such as a smartphone and/or a smart watch. The hearing device optionally comprises an antenna for converting one or more wireless input signals, e.g. a first wireless input signal and/or a second wireless input signal, to antenna output signal(s). The wireless input signal(s) may origin from external source(s), such as spouse microphone device(s), wireless TV audio transmitter, and/or a distributed microphone array associated with a wireless transmitter. The wireless input signal(s) may origin from another hearing device, e.g. as part of a binaural hearing system, and/or from one or more accessory devices.

The hearing device optionally comprises a radio transceiver coupled to the antenna for converting the antenna output signal to a transceiver input signal. Wireless signals from different external sources may be multiplexed in the radio transceiver to a transceiver input signal or provided as separate transceiver input signals on separate transceiver output terminals of the radio transceiver. The hearing device may comprise a plurality of antennas and/or an antenna may be configured to be operate in one or a plurality of antenna modes. The transceiver input signal optionally comprises a first transceiver input signal representative of the first wireless signal from a first external source.

The hearing device comprises a set of microphones. The set of microphones may comprise one or more microphones. The set of microphones comprises a first microphone for provision of a first microphone input signal and/or a second microphone for provision of a second microphone input signal. The set of microphones may comprise N microphones for provision of N microphone signals, wherein N is an integer in the range from 1 to 10. In one or more exemplary hearing devices, the number N of microphones is two, three, four, five or more. The set of microphones may comprise a third microphone for provision of a third microphone input signal.

The hearing device optionally comprises a pre-processing unit. The pre-processing unit may be connected to the radio transceiver for pre-processing the transceiver input signal. The pre-processing unit may be connected the first microphone for pre-processing the first microphone input signal. The pre-processing unit may be connected the second microphone if present for pre-processing the second microphone input signal. The pre-processing unit may comprise one or more ND-converters for converting analog microphone input signal(s) to digital pre-processed microphone input signal(s).

The hearing device comprises a processor for processing input signals, such as pre-processed transceiver input signal and/or pre-processed microphone input signal(s). The processor provides an electrical output signal based on the input signals to the processor. Input terminal(s) of the processor are optionally connected to respective output terminals of the pre-processing unit. For example, a transceiver input terminal of the processor may be connected to a transceiver output terminal of the pre-processing unit. One or more microphone input terminals of the processor may be connected to respective one or more microphone output terminals of the pre-processing unit.

The hearing device comprises a processor for processing input signals, such as pre-processed transceiver input signal(s) and/or pre-processed microphone input signal(s). The processor is optionally configured to compensate for hearing loss of a user of the hearing device. The processor provides an electrical output signal based on the input signals to the processor. Input terminal(s) of the processor are optionally connected to respective output terminals of the pre-processing unit. For example, a transceiver input terminal of the processor may be connected to a transceiver output terminal of the pre-processing unit. One or more microphone input terminals of the processor may be connected to respective one or more microphone output terminals of the pre-processing unit.

In accordance with the disclosure, there may be provided an earpiece for a hearing device, the earpiece comprising an ear canal part to be introduced into the ear canal of a user, the ear canal part comprising: an earpiece housing comprising a first end configured to be positioned medially inside the ear canal of the user, and a second end configured to be positioned laterally to the ear canal of the user, where the earpiece housing comprises a side wall extending from the first end to the second end, where the side wall at least partly defines a first volume inside the earpiece housing; a primary sensor where the primary sensor is positioned inside the first volume of the earpiece housing; where the side wall of the earpiece housing comprises a first pass-through area, and wherein the primary sensor is configured to measure a physiological parameter through the first pass-through area.

The provision of an earpiece housing having a first pass-through area in the side wall of the earpiece housing means that the primary sensor may be positioned inside the first volume of the earpiece housing, where the pass-through area allows the signals of the primary sensor to be transmitted from the sensor and measure signals that may e.g. be obtained from the skin surface of the user, and where the signals may be measured e.g. by reflection from the skin surface, past the pass-through area and be measured by the primary sensor. Thus the pass-through area may allow a sensor to be positioned inside the housing, where the pass-through area may be adapted to allow the signal to pass while maintaining the information contained in the signal.

The physiological parameter that may be received by the primary sensor may be a signal that represents a physiological state and/or physiological condition such as a heart rate, blood pressure, electrical signals (EMG/ECG) or other signals that may be measured from the body and/or the ear canal of the user.

The primary sensor may be an electrical component that may be capable of transforming physiological signals to electrical signals which contain a physiological parameter. In some cases the signal must be processed using analog or digital signal processing in order to extract the physiological parameter from the signal. Due to the fact that the primary sensor may be loaded with an electrical current, or that the sensor may be sensitive equipment it may be desired to prevent the sensor from coming into direct contact with the ear canal of the user. This may in part be due to the fact that the ear canal may have impurities that may disturb the signal transmission from the ear canal to the primary sensor or that the impurities may increase the risk that the primary sensor may be damaged by the impurities and/or fluids inside the ear canal. Thus, it may be a desire to move the sensor away from the skin surface of the ear canal and in a radial direction inwards into the inner volume of the earpiece housing.

Thus, in order to protect the primary sensor from the impurities inside the ear canal, or to improve the signal quality the side wall may be provided with a pass-through area, where the pass through area may be formed in such a way that it does not attenuate the contents of the signal. In one example where the primary sensor may be a optical sensor, the pass pass-through area may be a window, where the window may be transparent or translucent, so that the signal can travel through the window away from the primary sensor towards the skin surface and towards the primary sensor from the skin surface. The window may be provided as a translucent material such as a transparent layer, where the layer may e.g. made out of glass, polymer, or any type of material that may be suitable to place in the pass-through area.

It is to be understood that the use of the term "transparent" or "translucent" may be understood as being relative to the signal that is to be measured. I.e. for an optical signal a transparent material may be a material that allows the optical signal to pass through without losing the information contained in the signal. For an electrical signal the term transparent or translucent may mean that the material is electrically conductive, allowing the electrical signal to pass through the material without losing the information contained in the signal.

Thus, the pass through area may be provided in the form of a material that isolates the primary sensor from the surroundings, while still maintaining the capability of transmitting signals through the pass-through area. Thus, the primary sensor may be protected from the surroundings, and the risk of damaging the sensor may be reduced, compared to having an exposed primary sensor.

Within the context of the present disclosure, the terms "medial direction" and/or "lateral direction" is to be understood as standard anatomical terms of location, where medial direction means towards the longitudinal axis of the body, and where lateral direction may be seen as away from the longitudinal axis of the body, where both directions may be seen as being substantially in parallel to the frontal axis of the body, especially in relation to the discussion of directions inside the ear canal of the human body.

In one or more exemplary earpieces, the earpiece may comprise a receiver. The receiver may be positioned inside the earpiece and/or the earpiece housing. The receiver may be adapted to transmit sound to the eardrum of the user, when the earpiece is positioned inside the ear canal. The receiver may be positioned inside the first volume of the earpiece housing, so that the receiver is protected from the contaminants that may be inside the ear canal of the user.

In one or more exemplary earpieces, the receiver may be positioned in a receiver housing and the primary sensor is integrated in the receiver housing. The provision of a receiver housing, where the receiver housing comprises a receiver as well as a primary sensor may mean that the components for both the receiver and the primary sensor may be included in a housing. The integration of the receiver and the primary sensor in the receiver housing may reduce the total volume of components and circuitry inside the housing. A predefined volume of an earpiece housing may be seen as being defined by the structure and shape of the ear canal of the user, as the earpiece housing fills out a part of the volume of the ear canal. By providing a receiving housing in having both a receiver and a primary sensor means that a primary sensor may be introduced into an earpiece having a predefined volume, where the volume used by the receiving housing is similar to the volume already used by a receiver, and does therefore not take up more volume than a conventional receiver would, and will not enlarge the earpiece housing, as it already has a predefined volume, which is limited by anatomical structure of the ear canal.

Thus, by integrating the receiver and the primary sensor in a housing the space for components may be saved, and the components, connections and circuits may be integrated into a single housing, which may integrate the entire structure into a compact and small housing, which may fit inside the ear canal of the user.

In one or more exemplary earpieces, the receiver housing may be positioned inside the first volume of the earpiece housing. As the first volume is defined by at least parts of the side wall of the earpiece housing, where the side wall is positioned between the ear canal and the first volume when the earpiece is being used. By positioning the receiver housing inside the inner volume of the earpiece housing, the receiver housing may be protected from the environment which the earpiece is being used in, and where the earpiece housing defines the outer surface of the earpiece, while the receiver housing may be of any shape, provided that it fits inside the volume. The first volume may be shaped in the form of the receiver housing, so that the receiver housing may e.g. be inserted and removed from the first volume, and e.g. exchanged with a fresh one, e.g. in the situation where the receiver housing or parts thereof are defective or non-functional.

Figure 3:
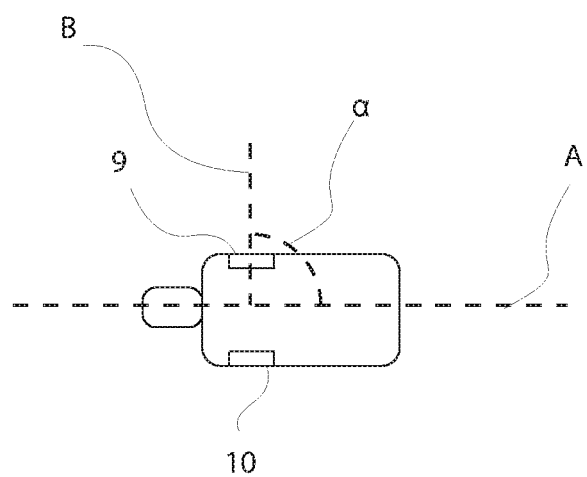
FIG. 3 shows a schematic view of the direction of transmission.

In one or more exemplary earpieces, the receiver housing may have a longitudinal axis extending in a direction from the first end to the second end of the primary housing and where the primary sensor is configured to measure the physiological parameter at an angle to the longitudinal axis, as may be seen in e.g. FIG. 3. This effectively means that the primary sensor is adapted to measure to the side of the receiver housing, so that the measurement may be obtained from a inner surface of the ear canal, where the inner surface of the ear canal is positioned substantially at a right angle to the longitudinal axis of the receiver housing. Thus, the longitudinal axis of the receiver housing may be parallel to a longitudinal axis of the earpiece, where the longitudinal axis of the receiver housing and/or the earpiece housing may be substantially parallel to a central axis of the ear canal. The central axis of the ear canal may from a medial direction of the ear canal in a lateral direction in a direction out of the ear canal, or may also be seen in the opposite direction, from the lateral part and in a medial direction towards the ear-drum of the user. [Possibly show a figure of the angles in FIG. 3, and the circular angle of one, two and/or three sensors in FIG. 4]

The angle between the longitudinal axis and the direction of measurement of the primary sensor may be any angle, where one example of an angle may e.g. be between 45-90 degrees relative to the longitudinal axis. The specific choice of angle may be anywhere between 1 and 90 degrees from the longitudinal axis, where the angle may be different from one type of sensor to the other. E.g. for the use of an optical sensor that is adapted to measure signals from the skin surface of the ear canal the optimal angle may be approximately 90 degrees, or somewhat close to a right angle to the skin surface, as the primary sensor sends out an optical signal and may register the reflection of the optical signal. Thus, it may be advantageous that the signal is both transmitted and received at a subsequent right angle to improve the measurement quality of the signal.

In one or more exemplary earpieces, the earpiece may comprise a secondary sensor, a tertiary sensor, or any subsequent sensor. The sensor may be a similar sensor to the primary sensor but may alternatively be a sensor measuring a different type of physical parameter than the primary sensor. The secondary or any subsequent sensor may be seen as a back-up sensor, so if the first sensor is not obtaining a useable signal, the second sensor may be used to obtain a useable signal. Furthermore, the secondary or any subsequent sensor may be used to increase the signal quality of the measurement, e.g. by averaging the signals relative to each other, or alternatively to increase the dimensional quality of the physiological parameter, where a first signal is measured using a first type of signal, while the second signal is a different type of signal, which is in the same phase as the first signal, where the second signal can e.g. provide further information about a different aspect of the physiological parameter.

In one or more exemplary earpieces, the first end may comprise a receiver opening. The first end may be adapted to be positioned close to the eardrum of the user, where it may be helpful to position the receiver opening close to the eardrum of the user, to reduce any possible sound attenuation from the receiver towards the eardrum.

In one or more exemplary earpieces, the earpiece may comprise a sound channel. The earpiece may be an earpiece that may be utilized together with a BTE hearing device, where the receiver is arranged in the BTE housing. Thus, the receiver may be connected to the earpiece via a hearing tube, and the sound may be transmitted towards the eardrum of the user via a sound channel inside the earpiece. Furthermore, the sound channel may terminate at the first end of the earpiece housing in a receiver opening, where the receiver opening provides sound communication to the sound channel, allowing the sound to be passed through the earpiece housing and towards the ear drum of the user, when the earpiece is being used.

In one or more exemplary earpieces, the side wall may comprise a second pass-through area. The presence of a secondary sensor, a tertiary sensor, or any subsequent sensor may cause that the earpiece housing may comprise a second pass-through area, a third pass-through area, or a subsequent pass-through area. Furthermore, the earpiece housing may comprise a second, third or a subsequent pass-through area for the primary sensor, should the presence of further pass through areas be advantageous to the measurement of the signals, e.g. if the signal is transmitted via one pass-through area but may be received in a second pass-through area.

In one or more exemplary earpieces, the the earpiece housing is a custom housing for a specific user corresponding to a 3D shape of the outer ear and/or the ear canal of the user. The provision of a custom housing may ensure that the earpiece fits the user in an optimal manner, where the outer shape of the custom housing may have surfaces that match the surface areas of the outer ear of the user. The custom housing may be formed or moulded using a 3D model of the ear and the ear canal of the user. The support structure may be part of the housing and may be formed together with the housing. This means that the support structure may be formed and structured optimally to hold the ear canal part in its position, as well as maintaining the support structure positioned in such a way, that the force applied between the superior part of the ear canal and the inferior concha cava is optimal for the specific user. I.e. that the force between these two anatomical parts is applied in an optimum manner, thereby reducing risk that the user will have fatigue in the ear when using the earpiece.

In one or more exemplary earpieces, the first side wall may be a non-elastic first surface. This effectively means that the side wall does not have to have an elastic part, which is adapted to bend or flex when force is applied to it but may be seen as a rigid contact surface. Thus, the side wall may have a contact surface that may be rigid. The rigidity of a contact surface may be viewed in terms of the use of the earpiece, in that it is very common to provide earpieces with a flexible member, that is adapted to enter the ear canal. Within the understanding of the present disclosure, the term rigidity means that prior and during use of the earpiece, the ear canal part maintains its shape, and the insertion of the ear canal part does not change the shape of the ear canal part inside the ear.

In one or more exemplary earpieces, the primary sensor may be a Photoplethysmogram (PPG) sensor. The PPG sensor may optically obtain a plethysmogram, which is a volumetric measurement of an organ. A PPG sensor may be obtained by using a pulse oximeter which illuminates the skin and measures changes in light absorption. A conventional pulse oximeter monitors the perfusion of blood to the dermis and subcutaneous tissue of the skin. The primary sensor may be utilized to measure the flow of blood below the skin, and the data received from the primary sensor may be utilized to extract data and process the data to obtain a physical data, which may represent a specific physiological condition of the user, such as a heart rate, or where it may be processed further to extract specific data that may show certain physical conditions. It may be advantageous to prevent e.g. daylight to pass between the skin of the user and the primary sensor. Thus, one of the advantages is that the primary sensor may be held in its correct position using the force transmitted via the support structure, so that the PPG sensor (primary sensor) is held in its correct position and does not move relative to the skin surface of the user. Any movement of the primary sensor relative to the skin surface may produce noise artefacts, that may cause the sensor signal, e.g. the PPG signal, to be unusable, or at least parts of the sensor signal to be too noisy to be used.

In one or more exemplary earpieces, the primary sensor may be an optical sensor, where the optical sensor may register an optical signal and extract a physiological parameter from the optical signal. The optical sensor may comprise an optical transmitter, where the transmitter transmits an optical signal into a skin surface of the user, where the optical sensor may measure the reflected optical signal transmitted by the optical transmitter.

In one or more exemplary earpieces, the first pass-through area is configured to be positioned between the primary sensor and the skin surface of the ear canal. Thus, the pass through area may provide a predefined distance from the primary sensor to the skin surface area, and may be positioned so that the signal is transmitted via the pass-through area into the skin, or from the skin surface and into the primary sensor.

In one or more exemplary earpieces, the first pass-through area is positioned in a radial direction relative to the primary sensor. The earpiece may have a longitudinal axis, which extends in along an axis that extends in the medial and lateral direction of the ear canal when the earpiece is positioned inside the ear canal. The primary sensor may be positioned at one position along the longitudinal axis, and the first pass-through area may be positioned in a radial direction relative to the primary sensor. The radial direction may be seen as being orthogonal to the longitudinal axis, and a radial axis that may be seen as intersecting with the longitudinal axis may intersect the primary sensor and the first pass-through area.

In one or more exemplary earpieces, the side wall at least partly encloses the first volume of the earpiece housing in a radial direction. Thus, the side wall of the earpiece may enclose the entire first volume of the earpiece, meaning that the side wall is an annular wall that extends around the entire radial periphery of the earpiece housing. The first pass through area may be an integral part of the side wall, or may be a cut-out of the side wall, or may be cut-out of the side wall, which may be covered in a transparent material which allows the signal to pass.

In one or more exemplary earpieces, the earpiece further may comprise an electrical wire connecting a receiver and/or the primary sensor to a BTE housing of the hearing device. The electrical wire may provide an electrical connection to the receiver and/or the primary sensor, and the electrical wire may extend from the earpiece to the BTE housing. The wire may be a stiff wire, that may be utilized to maintain the BTE housing in its position behind the ear of the user.

The present disclosure also relates to a receiver housing for a hearing device, the receiver housing may be configured to be introduced into the ear canal of a user, the receiver housing comprising: a receiver; a primary sensor, wherein the primary sensor is configured to measure a physiological parameter from the ear canal of the user.

In one or more exemplary receiver housings, the primary sensor is a Photoplethysmogram (PPG) sensor. The PPG sensor may optically obtain a plethysmogram, which is a volumetric measurement of an organ. A PPG sensor may be obtained by using a pulse oximeter which illuminates the skin and measures changes in light absorption. A conventional pulse oximeter monitors the perfusion of blood to the dermis and subcutaneous tissue of the skin. The primary sensor may be utilized to measure the flow of blood below the skin, and the data received from the primary sensor may be utilized to extract data and process the data to obtain a physical data, which may represent a specific physiological condition of the user, such as a heart rate, or where it may be processed further to extract specific data that may show certain physical conditions. It may be advantageous to prevent e.g. daylight to pass between the skin of the user and the primary sensor. Thus, one of the advantages is that the primary sensor may be held in its correct position using the force transmitted via the support structure, so that the PPG sensor (primary sensor) is held in its correct position and does not move relative to the skin surface of the user. Any movement of the primary sensor relative to the skin surface may produce noise artefacts, that may cause the sensor signal, e.g. the PPG signal, to be unusable, or at least parts of the sensor signal to be too noisy to be used.

The present disclosure also relates to a hearing device, where the hearing device may comprise an earpiece in accordance with the present disclosure.

FIG. 1 shows a perspective view of an exemplary earpiece 1 for a hearing device (not shown) where the earpiece 1 comprises an earpiece housing 2, where the earpiece housing comprises a side wall 3, having a first end 4 and a second end 5. The first end 4 comprises a receiver opening 6, which is adapted to be positioned in the vicinity of the eardrum when the earpiece 1 is positioned in the ear canal of the user. In this embodiment the second end 5 is shown as an open end, while in other embodiments the earpiece housing may be closed.

The dashed lines show the elements inside the earpiece housing 1, where the first volume 7 comprises a receiver housing 8, a primary sensor 9 and a secondary sensor 10, which are integrated in the receiver housing 8. The receiver housing further comprises a receiver 11 which is adapted to be lined up with the receiver opening 6 to allow sound to be transmitted from the first volume 7 of the earpiece housing and out of the receiver opening 6.

The primary sensor 9 and the secondary sensor 10 are positioned on a first side wall 12 and a second side wall 13 of the receiver housing, where the first side wall 12 is opposite the second side wall. The primary sensor 9 and the secondary sensor 10 may be optical sensors, e.g. a PPG sensor, that are adapted to transmit and receive optical signals to obtain a physiological parameter from the user. The side wall 3 of the earpiece housing 1 may be provided with a first window 14 and a second window 15 that are positioned adjacent to the primary sensor 9 and the secondary sensor 10, allowing the optical signal to pass via the windows 14, 15 and out of the earpiece housing 1 and into the skin surface of the ear canal, when the earpiece housing is positioned in the ear of the user. The remaining parts of the sidewall 3 may be opaque to the transfer of optical signals.

Figure 2:
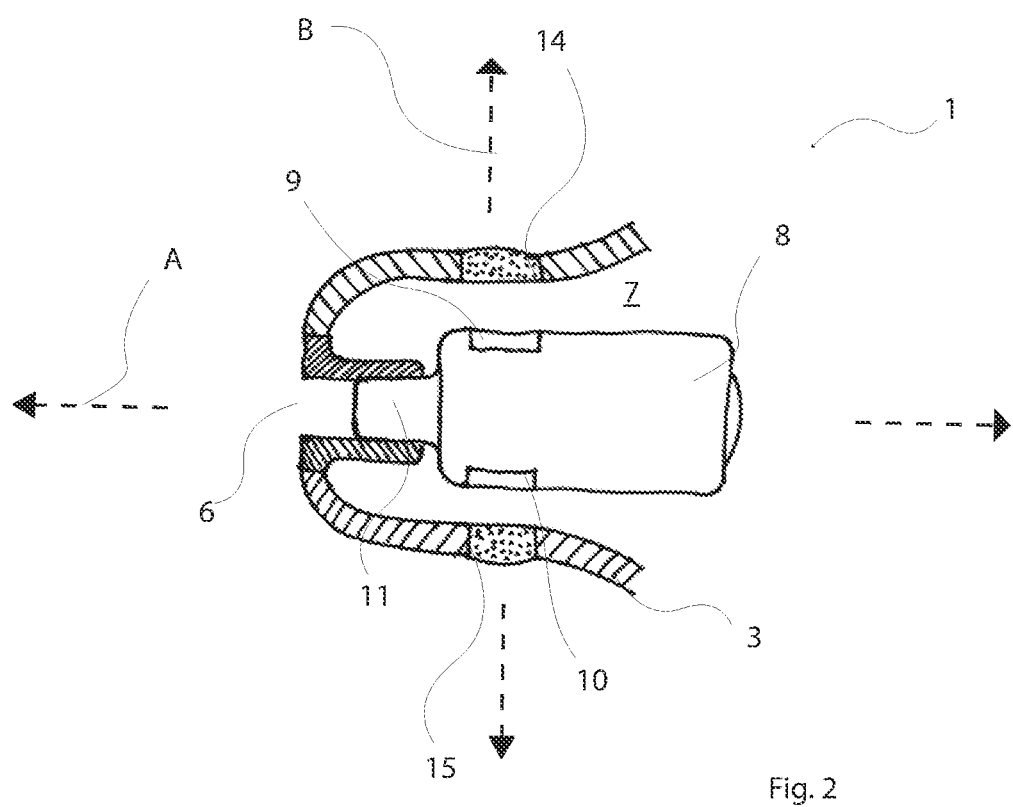
FIG. 2 is sectional view of a exemplary earpiece.

FIG. 2 shows a cross sectional view of the earpiece 1 of FIG. 1 along the axis II-II, where the cross sectional plane intersects the windows 14, 15 of the side wall 3. In this view it may be seen that the longitudinal axis A of the earpiece, extends from the first end 4 to the second end 5 of the earpiece housing 2, where the receiver is adapted to transmit sounds in a direction substantially parallel to the the longitudinal axis A. However, the primary sensor 9 and the secondary sensor 10 are adapted to transmit the measurement signal in a direction substantially parallel to the axis B (which extends in a radial direction), where the axis B is substantially at a right angle to the longitudinal axis B. Thus, the signals which are generated in the primary and the secondary sensors 9, 10, are transmitted in the direction B, where the signals pass through the pass-through areas 14, 15, and can come into contact with the skin surface of the ear canal (not shown) on the user. The signals area thereafter adapted to reflect from the skin of the ear canal, and return through the pass-through areas 14, 15 to be registered by the primary 9 and secondary sensors 10 upon return, where the signals may include a physiological parameter, which may represent a physical state/condition of the user.

FIG. 3 shows the receiver housing 8 of FIG. 1, where the receiver housing 8 comprises a primary sensor 9 and a secondary sensor 10, as well as a receiver 11. The longitudinal axis of the earpiece may be seen as axis A, where axis B may be seen as the direction of transmission for the primary sensor 9 and the secondary sensor 10. The angle $\alpha$ which is the angle between the longitudinal axis A and the direction of transmission B may be anywhere between 45-90 degrees, where it is advantageous that the signal may be transmitted towards the skin surface of the ear canal, in a different direction from the longitudinal axis, and that any reflection of a signal can return back to the primary and/or the secondary sensor, or alternatively to a photodetector that may be positioned inside the earpiece housing.

The positioning of the primary sensor 9 and the secondary sensor 10 along the longitudinal length of the receiver housing and/or the earpiece housing may be varied, where one sensor may be positioned further back than another sensor, or when there is only one sensor, the sensor may be positioned at any suitable longitudinal location of the receiver housing.

Figure 4A:
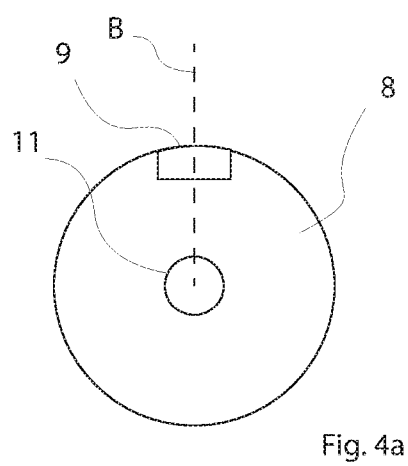
FIG. 4*a*, FIG. 4*b* and FIG. 4*c* shows a schematic view of the positioning of one or more sensors.
Figure 4B:
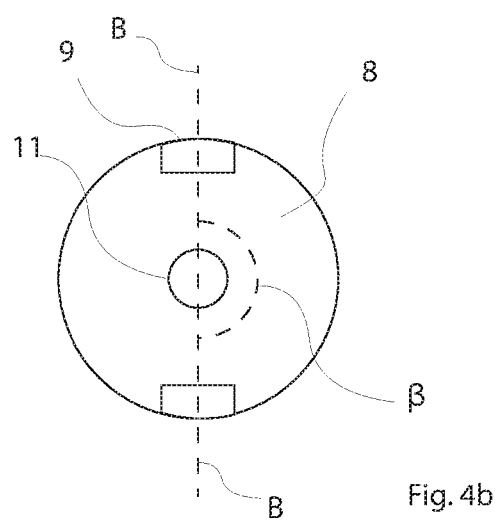
Figure 4C:
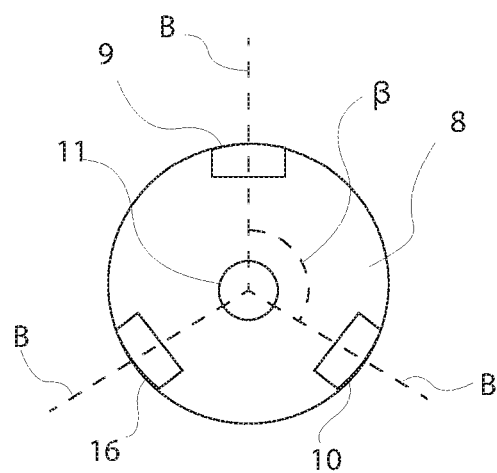

FIG. 4a-c shows a front view of a receiver housing 8, seen from the front where the positioning of the primary sensor and the transmission direction B in FIG. 4a may be seen as being at 0 degrees. When a second sensor is added, i.e. a secondary sensor 10, the secondary sensor 10 may be added at it may be added on the opposite side of the receiver housing, or at an angle $\beta$ that is approximately 180 degrees between the transmission directions B. In case the receiver housing also comprises a tertiary sensor 16, the three sensors 9, 10, 16 may be added at substantially equal angles, where the angle β may be seen as substantially 120 degrees between the transmission direction B. Alternatively, the secondary sensor and/or the tertiary sensor may be included on the receiver housing 8 at arbitrary angles relative to each other, should this be seen as being advantageous for the quality of the signal to be measured.

The pass-through areas of the earpiece housing may be adapted to positioned in the earpiece housing so that the pass-through areas intersect the direction of transmission B of the sensors 9, 10, 14, to allow the signal of the sensor to pass through the earpiece housing and into the skin surface of the ear canal.

In one example a large part of the sidewall may be transparent to allow transfer of optical signals, or the entire sidewall may be transparent to allow transfer of optical signals from the first volume and out of the earpiece housing. In one embodiment the earpiece housing as a whole may be provided in a transparent material, where a pass-through area may be provided in the form of one part of the side wall where the side wall may be polished in an area where the signal is to pass through the side wall, where the polishing may ensure that the signal may pass without significant attenuation and/or without losing the physiological information contained in the signal.

The diameter of the pass through area may be seen as being of a predefined size, where the diameter of the pass through area in the side wall may vary dependent on the specific type of primary sensor. In one embodiment the pass through area may have a diameter that is be approximately 1 mm or more, where the size may more specifically be around 2 mm or more.

In case the pass through area is a transparent element, such as a window, which may e.g. be of a transparent polymer which allows optical signals to pass through the pass-through area, the window may have a thickness that is approximately around 0.2 mm or more. In an alternative embodiment the thickness of the transparent polymer may be substantially the same as the thickness of the side wall of the earpiece housing.

In one example, where pass-through area may be a transparent window, the pass-through area may be in the form of a transparent lens, where the lens may be glued, pressed, heat-welded, embossed, injection moulded, 3D printed, into the side wall, where the side wall may be provided with an opening which fits the lens, or the side wall may be manufactured around the lens (i.e. by 3D printing or injection moulding). The lens, window, or transparent area may be fixed to the side wall from the inside of the side wall, or from the outside of the side wall.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

1 Earpiece
2 Earpiece housing
3 Side wall
4 First end
5 Second end
6 Receiver opening
7 First volume
8 Receiver housing
9 Primary sensor
10 Secondary sensor
11 Receiver
12 First side wall of receiver housing
13 Second side wall of receiver housing
14 First window
15 Second window
16 Tertiary Sensor
A Longitudinal axis
B Direction of transmission

The invention claimed is:

1. An earpiece for a hearing device, the earpiece comprising an ear canal part to be introduced into an ear canal of a user, the ear canal part comprising:

an earpiece housing comprising a first end configured to be positioned medially inside the ear canal of the user, and a second end configured to be positioned laterally to the ear canal of the user, wherein the earpiece housing comprises a side wall between the first end and the second end; and a primary sensor, wherein the primary sensor is positioned inside a first volume in the earpiece housing;

wherein the side wall of the earpiece housing comprises a first pass-through area, and wherein the primary sensor is configured to measure a physiological parameter through the first pass-through area of the side wall of the earpiece housing.

2. The earpiece of claim 1, wherein the earpiece comprises a receiver.

3. The earpiece of claim 2, wherein the receiver is positioned in a receiver housing, and wherein the primary sensor is integrated in, or is coupled with, the receiver housing.

4. The earpiece of claim 2, further comprising a receiver housing configured to house the receiver, wherein the receiver housing is positioned inside the earpiece housing.

5. The earpiece of claim 2, wherein the receiver is in a receiver housing, the receiver housing comprising a longitudinal axis extending in a direction from the first end to the second end of the earpiece housing, and wherein the primary sensor is configured to measure the physiological parameter at an angle relative to the longitudinal axis, wherein the angle is between 45-90 degrees relative to the longitudinal axis.

6. The earpiece of claim 1, wherein the first end of the earpiece housing comprises a receiver opening.

7. The earpiece of claim 1, further comprising a sound channel.

8. The earpiece of claim 1, wherein the side wall of the earpiece housing comprises a second pass-through area.

9. The earpiece of a hearing device according to claim 1, wherein the earpiece housing is a custom housing for the user.

10. The earpiece of claim 1, wherein the primary sensor is a Photoplethysmogram sensor.

11. The earpiece of claim 1, wherein the first pass-through area is configured to be positioned between the primary sensor and a surface of the ear canal.

12. The earpiece of claim 1, wherein the first pass-through area is located in a radial direction relative to the primary sensor.

13. The earpiece of claim 1, wherein the side wall of the earpiece housing circumferentially encloses at least a part of the first volume.

14. The earpiece of claim 1, wherein the side wall extends from the first end to the second end of the earpiece housing.

15. A hearing device comprising an earpiece of claim 1.

16. The earpiece of claim 1, further comprising a receiver housing inside the earpiece housing, wherein the primary sensor is coupled to the receiver housing.

17. The earpiece of claim 16, wherein the primary sensor that is coupled to the receiver housing is aligned with the pass-through area of the side wall of the earpiece housing.

18. The earpiece of claim 1, wherein the pass-through area comprises a lens.

19. The earpiece of claim 1, wherein the pass-through area has a thickness of 0.2 mm or more.

20. The earpiece of claim 1, wherein the pass-through area has a width of 1 mm or more.

21. The earpiece of claim 1, wherein the pass-through area comprises a material that is integral with the side wall.

22. The earpiece of claim 1, wherein the pass-through area comprises an opening of the side wall.

23. The earpiece of claim 22, wherein the pass-through area further comprises a transparent material covering the opening.

24. An apparatus, comprising:
a receiver housing for placement inside a space of a hearing device, wherein the space is inside an earpiece of the hearing device;
a receiver accommodated in the receiver housing; and
a primary sensor carried by the receiver housing, wherein the primary sensor is configured to measure a physiological parameter from an ear canal of a user.

25. The apparatus of claim 24, where the primary sensor is a Photoplethysmogram (PPG) sensor.

26. The apparatus of claim 24, wherein the primary sensor is at a peripheral part of the receiver housing.

27. The apparatus of claim 24, wherein the primary sensor is attached to the receiver housing.

28. An apparatus, comprising:
a receiver housing for placement inside a space of a hearing device;
a receiver accommodated in the receiver housing;
a primary sensor carried by the receiver housing, wherein the primary sensor is configured to measure a physiological parameter from an ear canal of a user; and
an earpiece housing having a pass-through area, wherein the primary sensor is aligned with the pass-through area.

29. An apparatus, comprising:
a receiver housing for placement inside a space of a hearing device;
a receiver accommodated in the receiver housing;
a primary sensor carried by the receiver housing, wherein the primary sensor is configured to measure a physiological parameter from an ear canal of a user; and
wherein the receiver housing defines a cavity for accommodating the receiver, and wherein the primary sensor has a sensor surface that is outside the cavity.

* * * * *